US00PP14763P2

(12) United States Plant Patent
Evers

(10) Patent No.: US PP14,763 P2
(45) Date of Patent: May 4, 2004

(54) HYBRID TEA ROSE PLANT NAMED 'TANRELCIG'

(50) Latin Name: *Rosa hybrida*
Varietal Denomination: TANrelcig

(75) Inventor: Hans-Jürgen Evers, Uetersen (DE)

(73) Assignee: Rosen Tantau Mathias Tantau Nachfolger, Uetersen (DE)

( * ) Notice: Subject to any disclaimer, the term of this patent is extended or adjusted under 35 U.S.C. 154(b) by 0 days.

(21) Appl. No.: 10/229,572

(22) Filed: Aug. 27, 2002

(51) Int. Cl.[7] ..... A01H 5/00

(52) U.S. Cl. ..... Plt./139
(58) Field of Search ..... Plt./139

(56) References Cited

PUBLICATIONS

UPOV ROM GTITM Computer Database, GTI JOUVE Retrieval Software 2003/02 citation for 'Tanrelcig'.*

* cited by examiner

*Primary Examiner*—Bruce R. Campell
*Assistant Examiner*—W C Haas
(74) *Attorney, Agent, or Firm*—Klarquist Sparkman, LLP

(57) ABSTRACT

Hybrid tea rose plant having a shiny red blossom color.

4 Drawing Sheets

Genus and species: Rosa hybrida.
Variety denomination: TANrelcig.

SUMMARY OF THE INVENTION

The present invention relates to a new and distinct variety of rose plant which was a spontaneous mutation of the variety TANkalcig (U.S. Plant Pat. No. 10,650) discovered by me in April, 1998 on a plant growing in a greenhouse at Uetersen, Germany.

Asexual reproduction of this new variety by budding, as performed at Uetersen, Germany, shows that the foregoing and all other characteristics and distinctions come true to form and are established and transmitted through succeeding propagations.

COMPARISON WITH PARENT

The rose variety TANrelcig differs from its parent principally in the color of the flower. In TANrelcig the upper surface of the petal is a shiny red ranging from Red Group 46B to Red Group 46A, and in TANkalcig the upper surface is Red Group 47A. In TANrelcig the reverse sides of the petals are Red Group 47A whereas in TANkalcig the reverse sides are Red Group 53A.

COMPARISON WITH SIMILAR VARIETY

The most similar rose variety to the candidate variety is its parent TANkalcig from which it differs as indicated above.

BRIEF DESCRIPTION OF THE ILLUSTRATIONS

The accompanying illustrations shows typical specimens of the vegetative growth and flowers of this new variety in different stages of development, depicted in color as nearly true as it is reasonably possible to make the same in color illustrations of this character.

DETAILED BOTANICAL DESCRIPTION

Figure 1:
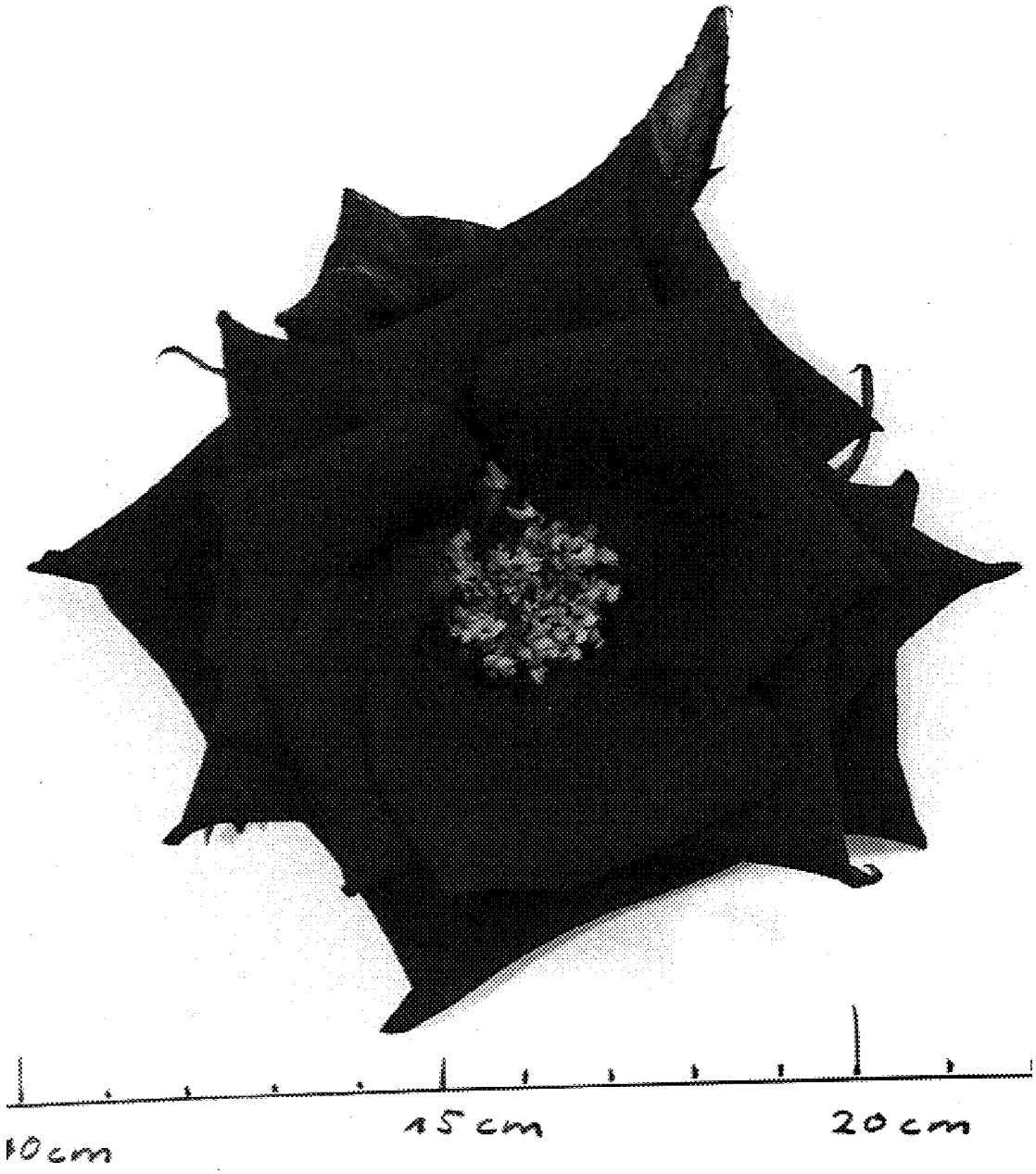
FIG. 1 is a top view of a fully opened blossom.
Figure 2:
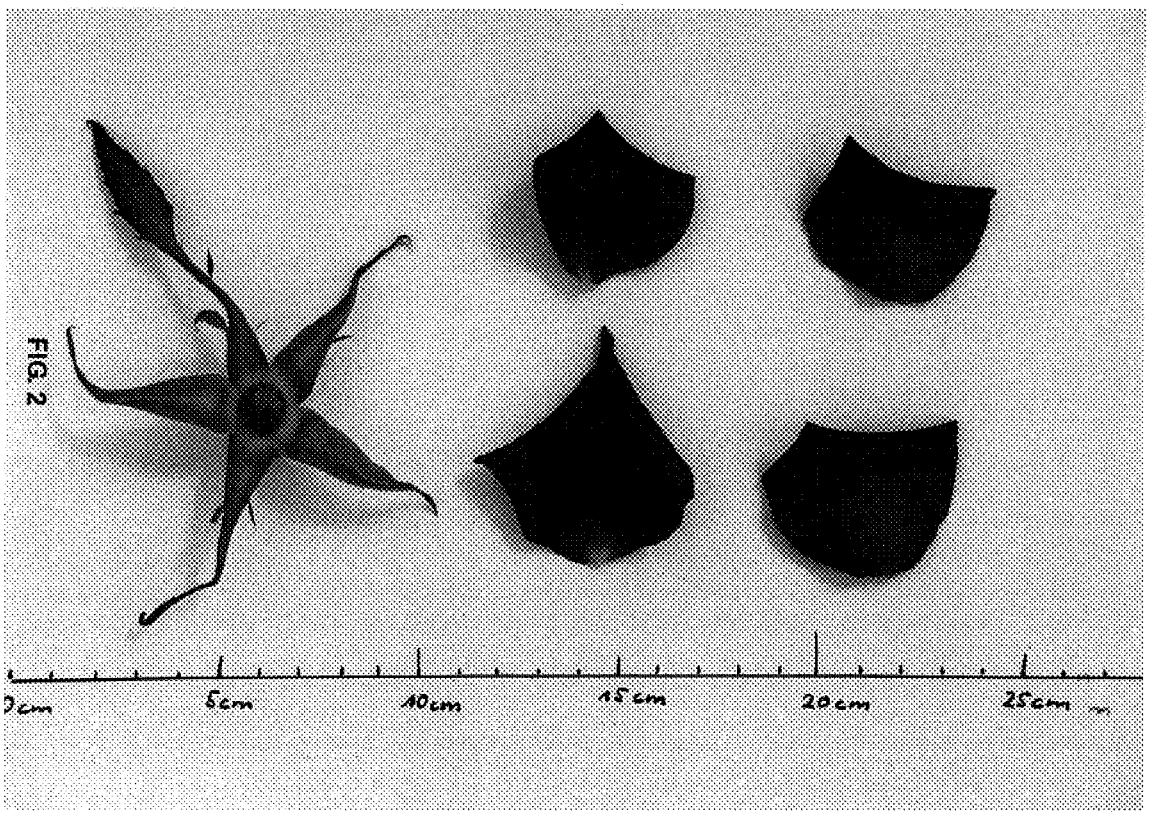
FIG. 2 is a view showing the upper and lower sides of some of the petals and the upper surface of the sepals.
Figure 3:
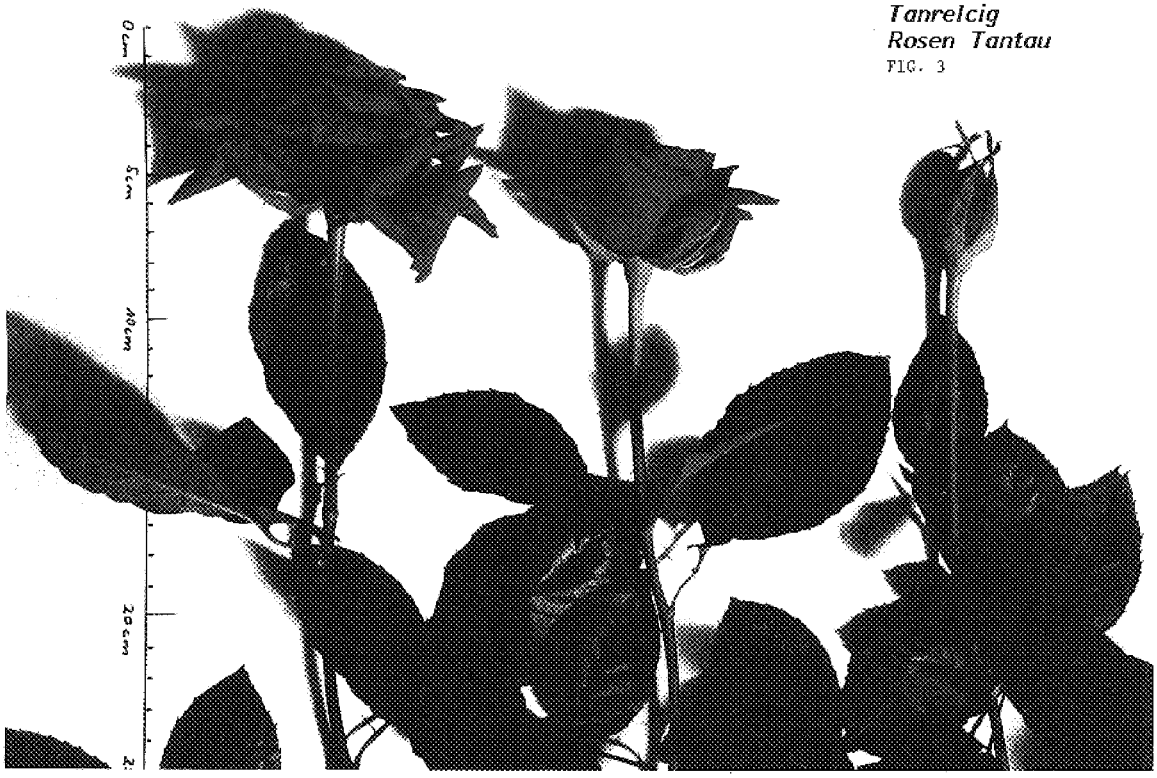
FIG. 3 is a view illustrating the opening sequence of the bud and showing leaflets on the flower stem.
Figure 4:
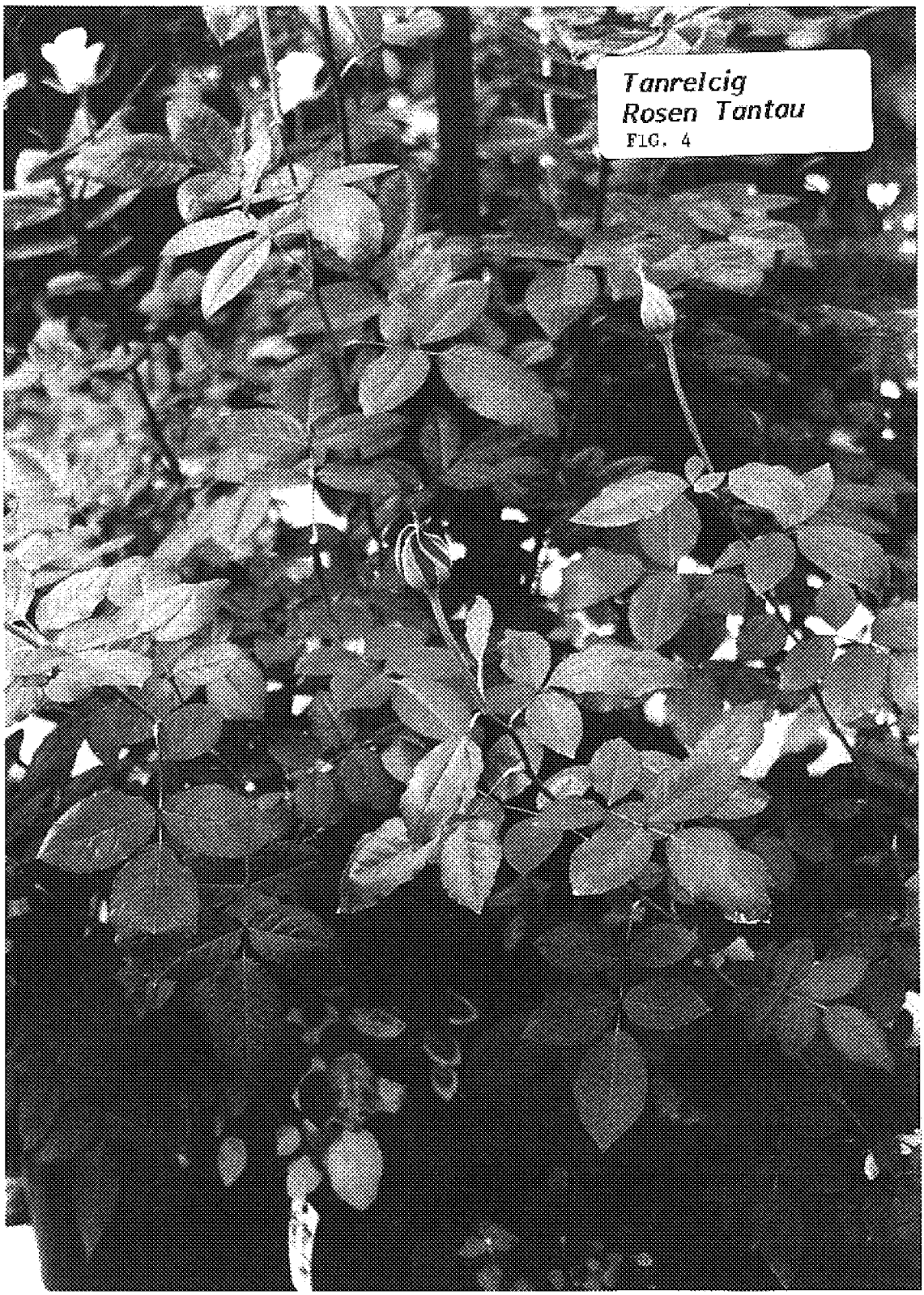
FIG. 4 is a more comprehensive view of several potted plants of TANrelcig showing the shape of the leaves and the leaflets and two buds in different stages of opening.

The following is a detailed description of my new rose cultivar with color descriptions using terminology in accordance with The Royal Horticultural Society (London) Colour Chart (1966), except where ordinary dictionary significance of color is indicated.

FLOWER

Observations made from plants of 3 years of age grown in a greenhouse environment at North Germany:

Blooming habit:
Bud:
- *Size.*—About 2.8 cm long and 1.4 cm in diameter when the petals start to unfurl.
- *Form.*—The bud form is globular.
- *Color.*—When sepals first divide, bud color is Red Group 45C. When half blown, the upper sides of the petals are Red Group 46A; and the lower sides of the petals are Red Group 46D.
- *Sepals.*—Color: Upper surface: Green Group 134A. Lower surface: Green Group 134B. Length: 6.2 cm. Width: 0.9 cm. Shape: Long, elongated. Surface texture: Smooth. There are three appendaged sepals. There are two unappendaged sepals with hairy edges.
- *Receptacle.*—Color: Green Group 134D. Shape: Funnel. Size: Medium., about 1 cm in diameter. Surface: Smooth.
- *Peduncle.*—Length: Medium, averaging about 7 cm. Surface: Smooth. Color: Green Group 134B. Strength: Erect.

Bloom:
- *Size.*—Average open diameter is about 9.5 cm.
- *Borne.*—Singly.

*Stems.*—Strength: Strong. Average length is about 75 cm and diameter is 0.6 cm.

*Form.*—When first open: Flat. Permanence: Outer petals curl back.

*Petalage.*—Number of petals under normal conditions: 31.

*Color.*—The upper sides of the petals are Red Group 46A to Red Group 46B. The reverse sides of the petals are Red Group 47A. The base of each petal has an Orange-White Group 159A spot. The major color on the upper side is Red Group 46A.

*Discoloration.*—The general tonality at the end of the first day: No fading. At the end of the third day: No fading.

*Fragrance.*—None.

Petals:

*Texture.*—Thick.

*Size.*—Length: 5.7 cm. Width: 4.8 cm.

*Surface.*—Rough.

*Shape.*—Nearly heart shaped.

*Margin.*—Not serrated but the ends of the petals curl back. Apex Shape: Pointed. Base Shape: Circular.

*Form.*—Edges slightly quilled.

*Arrangement.*—Irregular.

*Petaloids.*—Number: 9. Color: Same as petals.

*Persistence.*—Petals hang on and dry.

*Lastingness.*—On the plant: Very long (about 16 days). As a cut flower: Fair (about 12 days).

Reproductive parts:

*Stamens.*—Number: 72. Length: 1.1 cm. Anthers: Length: 0.2 cm. Color: Yellow-Orange Group 26A. Arrangement: Regular around styles. Filaments: Color: Orange-Red Group 31A. Length: 1.3 cm. Pollen: Color: Greyed-Orange Group 169A.

*Pistils.*—Number: 92. Length: 1.2 cm. Styles: Color: Red-Orange Group 32A. Length: 1.2 cm. Stigmas: Color: Orange-Red Group 35A. Length: 0.1 cm.

*Hips.*—None produced.

PLANT

*Form.*—Shrub.

*Growth.*—Very vigorous, upright.

*Mature plant.*—Height: 160 cm. Width: 35 cm. Age to maturity: 1 year.

*Rootstock.*—*Rosa canina inermis.*

Foliage: Number of leaflets on normal mid-stem leaves: 5.

*Size.*—Medium (15.4 cm long×11.6 cm wide).

*Quantity.*—Normal.

*Color.*—New foliage: Upper side: Green Group 135A. Lower side: Green Group 136C. Old foliage: Upper side: Green Group 136A. Lower side: Green Group 137B.

Leaflets:

*Size.*—About 5.9 cm long×3.3 cm wide.

*Shape.*—Oval.

*Base shape.*—Blunt.

*Apex shape.*—Pointed.

*Texture.*—Leathery.

*Edge.*—Serrated.

*Serrations.*—Single.

*Petiole.*—Color: Yellow-Green Group 147A overlaid with Red Group 42A.

*Petiole rachis.*—Color: Yellow-Green Group 147A overlaid with Red Group 42A. Underside: Smooth.

*Stipules.*—None.

*Disease resistance.*—Resistant to blackspot and susceptible to mildew and rust in a greenhouse under normal growing conditions.

*Pest resistance.*—Average.

*Vein color.*—Same as leaflet color.

*Venation pattern.*—Randomized.

Wood:

*New wood.*—Color: Green Group 137A. Bark: Smooth.

*Old wood.*—Color: Yellow-Green Group 148A. Bark: Rough.

Prickles:

*Quantity.*—On main canes from base: 10 per 20 cm stem length.

*Form.*—Hooked downward.

*Length.*—0.7 cm.

*Color when young.*—Green Group 133A overlaid with Greyed-Orange Group 172A.

*Color when mature.*—Greyed-Orange Group 166A.

Small prickles:

*Quantity.*—None.

Winter hardiness: Not tested.

I claim:

1. A new and distinct variety of rose plant of the hybrid tea class, substantially as herein shown and described, characterized particularly by its shiny red blossom color.

* * * * *

*Tanrelcig*
*Rosen Tantau*

Tanrelcig
Rosen Tantau